(12) United States Patent
Friedlander et al.

(10) Patent No.: US 8,694,333 B2
(45) Date of Patent: Apr. 8, 2014

(54) COHORT DRIVEN MEDICAL DIAGNOSTIC TOOL

(75) Inventors: Robert R. Friedlander, Southbury, CT (US); James R. Kraemer, Santa Fe, NM (US)

(73) Assignee: International Business Machines Corporation, Armonk, NY (US)

( * ) Notice: Subject to any disclaimer, the term of this patent is extended or adjusted under 35 U.S.C. 154(b) by 53 days.

(21) Appl. No.: 13/086,539

(22) Filed: Apr. 14, 2011

(65) Prior Publication Data

US 2012/0265550 A1    Oct. 18, 2012

(51) Int. Cl.
*G06Q 10/00*    (2012.01)

(52) U.S. Cl.
USPC .............................................. 705/2; 128/923

(58) Field of Classification Search
USPC .............................................. 705/2; 128/923
IPC .............................................. A61B 5/00,10/00
See application file for complete search history.

(56) References Cited

U.S. PATENT DOCUMENTS

| | | | |
|---|---|---|---|
| 5,551,436 A | 9/1996 | Yago | |
| 7,580,922 B2 | 8/2009 | Friedlander et al. | |
| 7,761,440 B2 | 7/2010 | Chow et al. | |
| 7,788,202 B2 | 8/2010 | Friedlander et al. | |
| 7,805,391 B2 | 9/2010 | Friedlander et al. | |
| 7,809,660 B2 | 10/2010 | Friedlander et al. | |
| 2002/0062226 A1 | 5/2002 | Ito et al. | |
| 2006/0200010 A1 | 9/2006 | Rosales et al. | |
| 2007/0143035 A1 | 6/2007 | Petruno | |
| 2007/0276777 A1* | 11/2007 | Krishnan et al. ............... | 706/46 |
| 2009/0094063 A1 | 4/2009 | Ennett | |
| 2009/0240523 A1 | 9/2009 | Friedlander et al. | |
| 2009/0259494 A1 | 10/2009 | Feder et al. | |
| 2009/0299766 A1* | 12/2009 | Friedlander et al. ............... | 705/3 |
| 2010/0010316 A1 | 1/2010 | Fueyo et al. | |
| 2010/0010363 A1 | 1/2010 | Fueyo et al. | |
| 2010/0010827 A1 | 1/2010 | Fueyo et al. | |
| 2010/0152885 A1 | 6/2010 | Regan et al. | |
| 2010/0241472 A1 | 9/2010 | Hernandez | |
| 2010/0251117 A1 | 9/2010 | Baughman et al. | |
| 2011/0060737 A1 | 3/2011 | Cardella et al. | |
| 2012/0316891 A1 | 12/2012 | Friedlander et al. | |
| 2012/0317127 A1 | 12/2012 | Friedlander et al. | |

FOREIGN PATENT DOCUMENTS

JP    2010-017519    1/2010
WO    2009103156 A1    8/2009

OTHER PUBLICATIONS

Guide to History Taking and Examination, Oct. 2009, University College London Medical School, p. 2-9.*
Definition of "attributable," vocabulary.com, Apr. 2013.*
Owen Bond, Tinnitus and Vitamin Deficiencies, Livestrong.com, Apr. 16, 2011.*

(Continued)

*Primary Examiner* — John Pauls
*Assistant Examiner* — Jason Tiedeman
(74) *Attorney, Agent, or Firm* — John R. Pivnichny; Law Office of Jim Boice

(57) ABSTRACT

A computer implemented method, system, and/or computer program products derives a medical diagnosis for a patient. A current description of a patient is matched to a cohort of persons who each have a substantially similar description as the patient. Possible medical diagnoses, which have been accurate for members of the cohort, are presented for the patient. If one of the secondary medical diagnoses has an unacceptably high potential for an unacceptable outcome if improperly treated, then additional tests are run to rule out that secondary medical diagnosis.

20 Claims, 3 Drawing Sheets

(56) References Cited

OTHER PUBLICATIONS

U.S. Appl. No. 13/159,076—Final Office Action mailed May 10, 2013.

Fundakowski et al., "Disfigurement Perception, Quality of Life, and Mental Health in the Post-Treatment Head and Neck Cancer Patient", University of Miami—Miller School of Medicine, N.D., pp. 1.

Anonymous, "Loss of Mobility Found to Impact Quality of Life and Emotional and Financial Health of Most People Living With Multiple Sclerosis," Acorda Therapeutics, Inc., Mar. 25, 2008, pp. 1-4.

Hertenstein et al., "Quality of Life Changes Following Inpatient and Outpatient Treatment in Obsessive-Compulsive Disorder: A Study With 12 Months Follow-Up," Annals of General Psychiatry, 2013, 12:4, pp. 1-9.

Katz, "The Impact of Pain Management on Quality of Life", Proceedings From the Roundtable on "The Role of Coxibs in Successful Pain Management", Journal of Pain and Symptom Management, vol. 24, No. 1S, Jul. 2002, pp. S38-S47.

Ziaian et al., "Treatment Burden and Health-Related Quality of Life of Children With Diabetes, Cystic Fibrosis and Asthma", Journal of Paediatrics and Child Health 42, 2006, pp. 596-600.

Anonymous, "Treat", dictionary.com, Apr. 2013, pp. 1-3.

U.S. Appl. No. 13/158,858—Notice of Allowance mailed Jun. 10, 2013.

Pettitt et al., "Comparison of World Health Organization and National Diabetes Data Group Procedures to Detect Abnormalities of Glucose Tolerance During Pregnancy", Diabetes Care, vol. 17, No. 11, Nov. 1994, pp. 1264-1266.

U.S. Appl. No. 13/159,076, Robert R. Friedlander et al., Non-Final Office Action Mailed Nov. 29, 2012.

U.S. Appl. No. 13/158,858, Robert R. Friedlander et al., Non-Final Office Action Mailed Nov. 21, 2012.

U.S. Appl. No. 13/939,620—Notice of Allowance Mailed Sep. 30, 2013.

U.S. Appl. No. 13/159,076—Examiner'S Answer Mailed Dec. 9, 2013.

\* cited by examiner

US 8,694,333 B2

COHORT DRIVEN MEDICAL DIAGNOSTIC TOOL

BACKGROUND

The present disclosure relates to the field of computers, and specifically to the use of computers in the field of medicine. Still more particularly, the present disclosure relates to the use of computers in deriving medical diagnoses.

Deriving a medical diagnosis for a patient is often an inexact science. That is, rather than initially identifying a particular disease, the process of medical diagnosing often takes on the task of eliminating candidate diseases until a most likely candidate for the particular disease is identified. This process typically focuses on results of a physical examination and lab tests of the patient. However, such traditional diagnostic processes often misdiagnose the disease, with the occasional result of devastating consequences.

BRIEF SUMMARY

A computer implemented method, system, and/or computer program products derives a medical diagnosis for a patient. A current description of a patient is matched to a cohort of persons who each have a substantially similar description as the patient. Possible medical diagnoses, which have been accurate for members of the cohort, are presented for the patient. If one of the secondary medical diagnoses has an unacceptably high potential for an unacceptable outcome if improperly treated, then additional tests are run to rule out that secondary medical diagnosis.

DETAILED DESCRIPTION

Figure 1:
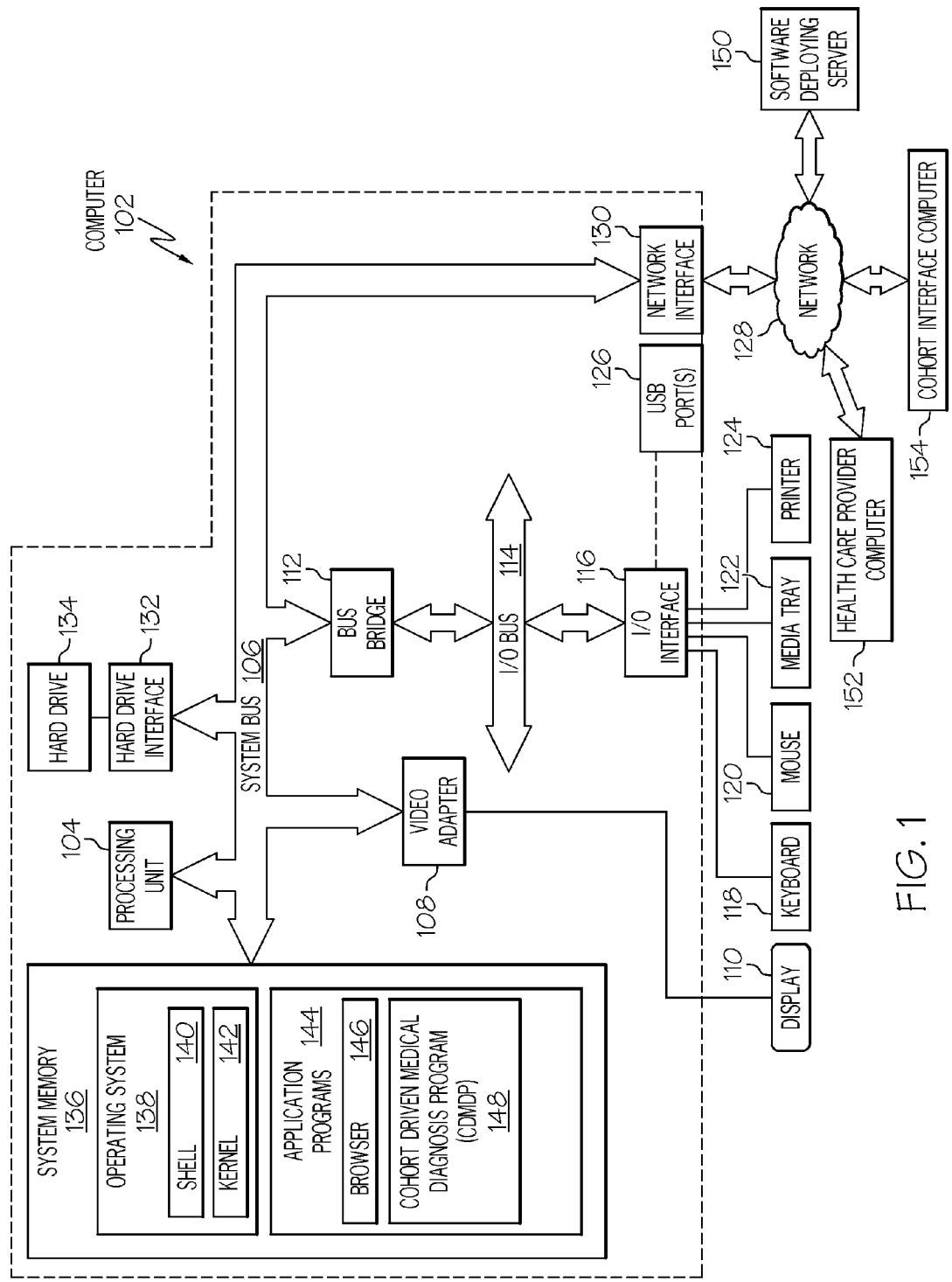
FIG. 1 depicts an exemplary computer in which the present disclosure may be implemented.

As will be appreciated by one skilled in the art, aspects of the present invention may be embodied as a system, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electro-magnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including, but not limited to, wireless, wireline, optical fiber cable, RF, etc., or any suitable combination of the foregoing.

Computer program code for carrying out operations for aspects of the present invention may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described below with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

With reference now to the figures, and in particular to FIG. 1, there is depicted a block diagram of an exemplary computer 102, which may be utilized by the present invention. Note that some or all of the exemplary architecture, including both depicted hardware and software, shown for and within computer 102 may be utilized by software deploying server 150, a health care provider computer 152, and/or a cohort interface computer 154.

Computer 102 includes a processing unit 104 that is coupled to a system bus 106. Processing unit 104 may utilize one or more processors, each of which has one or more processor cores. A video adapter 108, which drives/supports a display 110, is also coupled to system bus 106. System bus 106 is coupled via a bus bridge 112 to an input/output (I/O) bus 114. An I/O interface 116 is coupled to I/O bus 114. I/O interface 116 affords communication with various I/O devices, including a keyboard 118, a mouse 120, a media tray 122 (which may include storage devices such as CD-ROM drives, multi-media interfaces, etc.), a printer 124, and external USB port(s) 126. While the format of the ports connected to I/O interface 116 may be any known to those skilled in the art of computer architecture, in one embodiment some or all of these ports are universal serial bus (USB) ports.

As depicted, computer 102 is able to communicate with a software deploying server 150 using a network interface 130. Network 128 may be an external network such as the Internet, or an internal network such as an Ethernet or a virtual private network (VPN).

A hard drive interface 132 is also coupled to system bus 106. Hard drive interface 132 interfaces with a hard drive 134. In one embodiment, hard drive 134 populates a system memory 136, which is also coupled to system bus 106. System memory is defined as a lowest level of volatile memory in computer 102. This volatile memory includes additional higher levels of volatile memory (not shown), including, but not limited to, cache memory, registers and buffers. Data that populates system memory 136 includes computer 102's operating system (OS) 138 and application programs 144.

OS 138 includes a shell 140, for providing transparent user access to resources such as application programs 144. Generally, shell 140 is a program that provides an interpreter and an interface between the user and the operating system. More specifically, shell 140 executes commands that are entered into a command line user interface or from a file. Thus, shell 140, also called a command processor, is generally the highest level of the operating system software hierarchy and serves as a command interpreter. The shell provides a system prompt, interprets commands entered by keyboard, mouse, or other user input media, and sends the interpreted command(s) to the appropriate lower levels of the operating system (e.g., a kernel 142) for processing. Note that while shell 140 is a text-based, line-oriented user interface, the present invention will equally well support other user interface modes, such as graphical, voice, gestural, etc.

As depicted, OS 138 also includes kernel 142, which includes lower levels of functionality for OS 138, including providing essential services required by other parts of OS 138 and application programs 144, including memory management, process and task management, disk management, and mouse and keyboard management.

Application programs 144 include a renderer, shown in exemplary manner as a browser 146. Browser 146 includes program modules and instructions enabling a world wide web (WWW) client (i.e., computer 102) to send and receive network messages to the Internet using hypertext transfer protocol (HTTP) messaging, thus enabling communication with software deploying server 150 and other computer systems.

Application programs 144 in computer 102's system memory (and, in one embodiment, software deploying server 150's system memory, health care provider's computer 152) also include a cohort driven medical diagnosis program (CDMDP) 148. CDMDP 148 includes code for implementing the processes described below, including those described in FIGS. 2-3. In one embodiment, computer 102 is able to download CDMDP 148 from software deploying server 150, including in an on-demand basis, wherein the code in CDMDP 148 is not downloaded until needed for execution to define and/or implement the improved enterprise architecture described herein. Note further that, in one embodiment of the present invention, software deploying server 150 performs all of the functions associated with the present invention (including execution of CDMDP 148), thus freeing computer 102 from having to use its own internal computing resources to execute CDMDP 148.

The hardware elements depicted in computer 102 are not intended to be exhaustive, but rather are representative to highlight essential components required by the present invention. For instance, computer 102 may include alternate memory storage devices such as magnetic cassettes, digital versatile disks (DVDs), Bernoulli cartridges, and the like. These and other variations are intended to be within the spirit and scope of the present invention.

Figure 2:
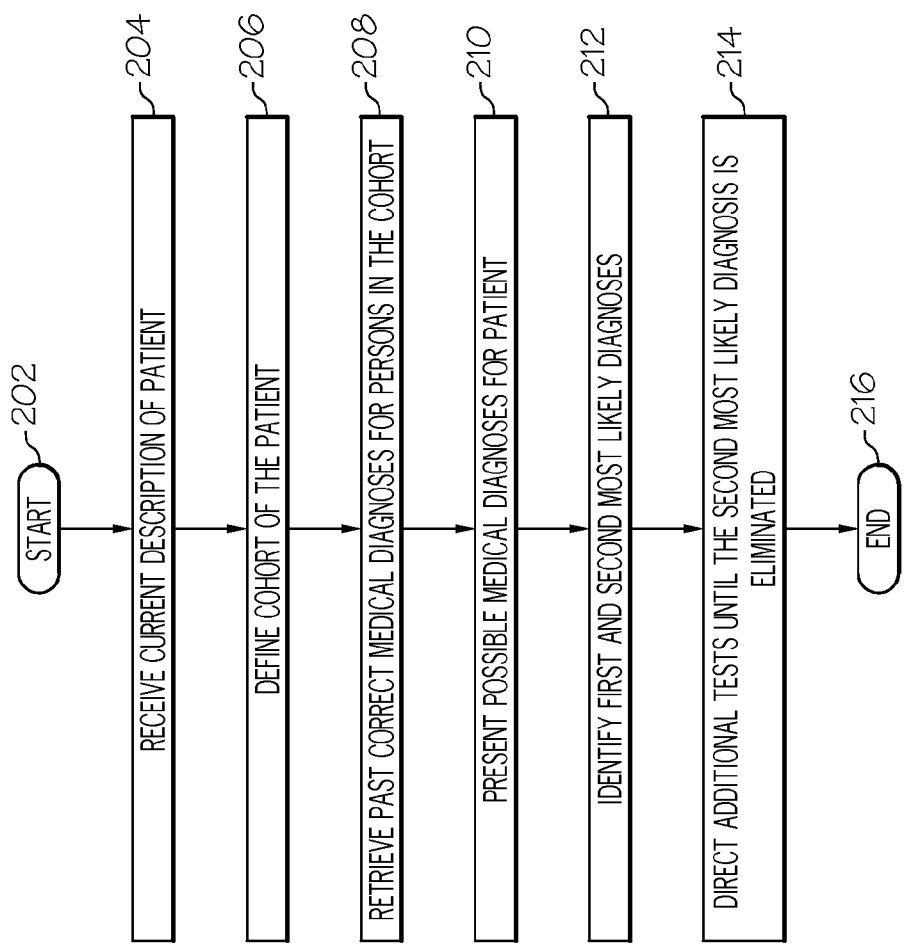
FIG. 2 is a high level flow chart of one or more exemplary steps performed by a processor to derive a medical diagnosis for a patient.

With reference now to FIG. 2, a high level flow chart of one or more exemplary steps performed by a processor to derive a medical diagnosis for a patient is presented. After initiator block 202, a current description of a patient is received by a computer, such as computer 102 depicted in FIG. 1, from a computer such as the health care provider computer 152 (also shown in FIG. 1). In one embodiment, this current description includes, but is not necessarily limited to, a current complaint of the patient (i.e., what discomfort, limitations, medical anomalies are being disclosed by the patient); a medical history of the patient (i.e., a history of past medical conditions, lab test results, examination results, etc.), a current lab test result (e.g., blood work, urinalysis, x-rays, etc.) for the patient, a current physical examination result (e.g., complaints voiced by the patient, observations made by the health care provider, etc.) for the patient, a demographic description (e.g., age, sex, ethnicity, occupation, location of current residence, current income level, etc.) of the patient, a travel history (e.g., when and where the patient has traveled during some predefined period of time) of the patient; and any experienced traumas by the patient that are unattributable to the current complaint of the patient (e.g., the patient may have recently broke a bone in her arm, yet is complaining of tinnitus, which is unattributable to the broken arm).

Note that in one embodiment the medical history of the patient(s) includes previous treatments for prior conditions. Examples of such treatments for prior conditions include, but are not limited to, surgery, chemotherapy for cancer, radiation treatment for cancer, heart bypass surgery, pharmaceutical regimens, etc. Examples of non-treatment exposures include, but are not limited to, traumatic brain injury due to exposure to severe force (i.e., an open or closed head injury from an explosion), exposure to a chemical agent, which may or may not have resulted in an obstructive pulmonary disease, etc. In the prior art, such treatments and/or exposures prevent persons from participating in pharmaceutical trials and different research protocols, and thus would not be included in a cohort. However, in one embodiment of the present invention, this cumulative history of insults to the body and their associated treatment are precisely what defines the cohort, such that there is an inclusion of as many of these people as possible. Thus, while prior art cohorts are defined as a limited group according to a certain pre-defined medical condition, the present application defines a cohort as a group of persons that share a wide range of adverse, cumulative, and multiplicative features that match the current patient. In one embodiment, these features are a combination of common complaints, diagnoses, treatments, injuries, demographics, travel history, unrelated trauma, and etc. found for members of the cohort (as well as the current patient).

As described in block 206, a processor then defines/retrieves/matches the patient to a particular cohort. This cohort is made up of persons who each have a substantially similar lab test result, physical examination result, demographic description, and travel history as the patient. For example, assume that a database (not shown) for a group (cohort) of 100 persons is found in a system such as the cohort access computer 154 shown in FIG. 1. This database reveals that every member of this cohort has, within a predefined range, a substantially similar lab test result, physical examination result, demographic description, and travel history as the patient. It is this substantial similarity that places these 100 persons into the cohort. As described in block 208, the processor then retrieves past accurate medical diagnoses for persons in the cohort. In one embodiment, this retrieval produces a single diagnosis that was accurate for all members of the cohort. In another embodiment, this retrieval produces multiple medical diagnoses, rather than a single diagnosis. These multiple medical diagnoses are then presented to the health care provider of the current patient as possible medical diagnoses for the patient (block 210).

As described in block 212, the processor then identifies a most likely diagnosis for the patient and a second most likely diagnosis for the patient. The most likely diagnosis is the diagnosis that is truly the most likely (for reasons described below), while the second most likely diagnosis is not as likely as the most likely diagnosis, but is the first runner-up when compared to the other possible medical diagnoses that have been presented. Note that the most likely diagnosis has a first probability of a first unacceptable outcome if improperly treated; the second most likely diagnosis has a second probability of a second unacceptable outcome if improperly treated; and the second probability is greater than the first probability. For example, consider the different diagnoses charted in chart 300 in FIG. 3.

Chart 300 depicts the probability of different diagnoses 302-310 being correct. That is, the combined areas under all curves depicting the different diagnoses 302-310 equal 1.0 (100%). Thus in one example depicted in FIG. 3, diagnosis 302 may have a probability of 50% of being accurate for the present patient; diagnosis 304 may have a probability of 20% of being accurate for the present patient, and diagnoses 306-310 may each have a 10% probability of being accurate for the present patient. Note that besides depicting the probability of a particular diagnosis being accurate for the present patient, the curves depicting the different diagnoses 302-310 also show the likelihood of unacceptable outcomes 312 if the disease associated with a particular diagnosis is not properly (timely, using the proper medicine/surgery/etc.) treated. Thus, for the disease associated with (identified/diagnosed by) diagnosis 302, an unacceptable outcome will occur 7% of the time if that disease is improperly treated, while acceptable outcomes 314 occur 93% of the time, either with or without proper treatment. However, for the disease associated with diagnosis 304, an unacceptable outcome will occur 50% of the time if that disease is improperly treated.

Note that an outcome is deemed unacceptable if the results meet some predefined criteria for that patient, disease, etc. Examples of such predefined criteria include death of the patient, an inordinate level of disability, an inordinate level of pain, the inability to provide additional treatment, and irreversible conditions. An inordinate level of disability or pain is that level that goes beyond normal disability/pain that is typically associated with a particular medical condition. An example of an inability to provide addition treatment is a surgical procedure that, if done improperly the first time, cannot be redone (or undone) later. Another example of the inability to provide additional treatment is the administration of certain pharmaceuticals, which if improper/ineffective, nonetheless preclude, for pharmacological reasons, administering other pharmaceuticals. An irreversible condition is similar to an inability to provide addition treatment. An example of such an irreversible condition is incorrectly removing a misdiagnosed and yet healthy organ, limb, etc.

Note that in one embodiment, an outcome may be deemed unacceptable, even if reversible, if the cost to correct the outcome is greater than a permissible upper limit. This cost may be monetary, physical (i.e., correcting the problem will cause and/or exacerbate other medical conditions of the patient), emotional (i.e., correcting the problem will cause unacceptable levels of stress on the patient and/or the patient's family), etc.

Figure 3:
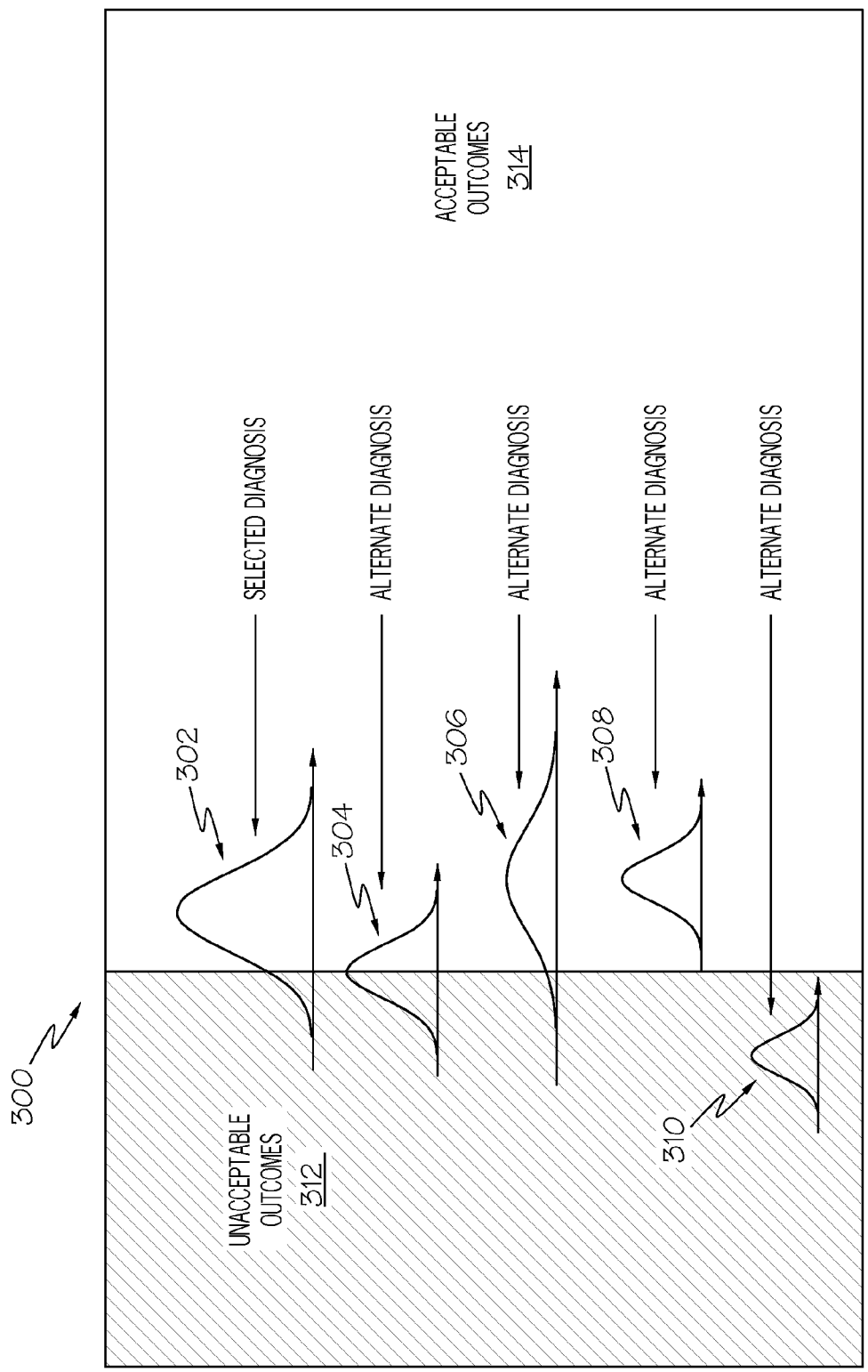
FIG. 3 is a chart depicting multiple alternative diagnoses that have various unacceptable outcome levels.

Note also diagnoses 308 and 310 in FIG. 3. Diagnosis 310 is for a disease that, if not timely and properly treated, will always have unacceptable outcomes. Examples of diseases associated with such a diagnosis include severe anaphylaxis, internal bleeding, sepsis, etc. Other diseases, however, even if not properly diagnosed and/or treated, may have no unacceptable outcome, such as the disease associated with the graph for diagnosis 308. Examples of such diseases include conditions such as temporary indigestion, minor muscle aches, etc.

Returning to FIG. 2, the identification of and ranking of different diagnoses, as described/suggested in block 212, can be performed in various manners. In one embodiment, a processor merely identifies a most frequent diagnosis from past accurate medical diagnoses for persons in the cohort. That is, if 70% of the members of a cohort having the same traits/history/characteristics/symptoms/etc. as the current patient have Disease A, then this is deemed the most likely diagnosis. In another embodiment, however, the process is more complex. More specifically, in this embodiment the process begins with the processor mapping different permutations of the lab test result, physical examination result, demographic description, and travel history for persons in the cohort to past accurate medical diagnoses. That is, while members of the cohort, by definition, will exhibit/have/display all of the same traits/history/characteristics/symptoms/etc. as the current patient, there will still be variations in "how much" (i.e., what "quantity") of each of these factors a member of the cohort who was diagnosed with a particular disease had. For example, one shared trait among the cohort may be the smoking of tobacco cigarettes. However, among the patients who share that trait, some may smoke only 2 cigarettes per day, while others smoke 2 packs of cigarettes (40) per day. In another example, other members of the cohort may share genetic markers with the current patient, however, some may share 50 genetic markers and others may share only 2 genetic markers. The processor uses these quantities of factors to identify a best fit permutation from the different permutations for persons in the cohort. This best fit permutation is the combination/quantity of factors held by one or more members of the cohort that matches the factors held by the current patient. Based on this permutation matching, the processor is then able to identify the most likely diagnosis according to which diagnosis is mapped to the best fit permutation.

In one embodiment, the process described in block 212 also includes identifying a third most likely diagnosis for the patient from the plurality of possible medical diagnoses. This third most likely diagnosis has a third probability of a third unacceptable outcome if improperly treated. This third probability is less than the first probability, and thus the processor eliminates this third most likely diagnosis as the candidate diagnosis for the patient. For example, consider the disease associated with the diagnosis described by graph 306. As suggested by the area under this graph, this diagnosis 306 may present a high probability of being correct. However, since the percentage of unacceptable outcomes 312 associated with this disease/diagnosis/graph are negligible, then this diagnosis 306 may be ignored, just as the disease associated with the diagnosis 308 can be ignored (due to the lack of any adverse and/or unacceptable outcomes from improper treatment of the disease associated with that diagnosis).

Returning now to FIG. 2, as described in block 214, the processor then directs (issues instructions to perform) additional tests on the patient until the second most likely diagnosis is eliminated as a candidate diagnosis for the patient. That is, as long as there is still a secondary diagnosis in play, which has an associated unacceptable outcome that is higher than that of the most likely diagnosis, then additional tests are run until that other secondary diagnosis is ruled out. If that other secondary diagnosis is never ruled out after some predetermined length of time, number of tests, cost, etc., then additional tests are run on the "most likely" diagnosis in order to rule it out. The process ends at terminator block 216.

In certain scenarios, additional diagnoses must also be evaluated. For example, assume that the processor has determined that the second unacceptable outcome is a certainty regardless of any medical intervention (e.g., an incurable disease, an inoperable condition, etc.), if a confirmation of the second most likely diagnosis is reached. In this scenario, the processor eliminates the second most likely diagnosis as the candidate diagnosis for the patient, since no benefit would be gained from diagnosing this condition, meaning, there is no proper medical treatment available to avert or reverse the second unacceptable outcome. Therefore, resources used (tests, money, time, etc.) to confirm the second most likely diagnosis are considered wasteful when the resources could instead be devoted to confirming or eliminating an alternate diagnosis that is treatable within predetermined limits. Thus, the resources of the processor are used to identify a third most likely diagnosis for the patient from the plurality of possible medical diagnoses. This third most likely diagnosis has a third probability of a third unacceptable outcome if improperly treated. This third probability is less than the second probability, but is greater than the first probability. After identifying this third diagnosis, the processor directs (issues instructions to perform) additional tests on the patient until the third most likely diagnosis is eliminated as a candidate diagnosis for the patient.

As described herein, the present invention provides a significant and novel improvement over the prior art. That is, the present invention is able to present possible medical diagnoses that are primarily driven by a commonality with a cohort. For example, factors such as eating a particular food, sleeping during certain times of the day, watching certain types of television, etc. would not ordinarily be asked during a medical workup, since most health care providers would see no correlation between such factors and a particular disease/diagnosis. Nonetheless, by the very definition of the cohort, together all of the members experience a set of diseases that have been identified in the past by accurate medical diagnoses. The underlying cause for such diseases may eventually turn out to be these factors (eating a particular food, sleeping during certain times of the day, watching certain types of television, etc.). Nonetheless, accurate diagnoses can be presented/suggested for the present patient, even if the underlying etiology of the disease is not known/understood.

The flowchart and block diagrams in the figures illustrate the architecture, functionality, and operation of possible implementations of systems, methods and computer program products according to various embodiments of the present disclosure. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of various embodiments of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

Note further that any methods described in the present disclosure may be implemented through the use of a VHDL (VHSIC Hardware Description Language) program and a VHDL chip. VHDL is an exemplary design-entry language for Field Programmable Gate Arrays (FPGAs), Application Specific Integrated Circuits (ASICs), and other similar electronic devices. Thus, any software-implemented method described herein may be emulated by a hardware-based VHDL program, which is then applied to a VHDL chip, such as a FPGA.

Having thus described embodiments of the invention of the present application in detail and by reference to illustrative embodiments thereof, it will be apparent that modifications and variations are possible without departing from the scope of the invention defined in the appended claims.

What is claimed is:

1. A computer implemented method of deriving a medical diagnosis for a patient, the computer implemented method comprising:
a processor receiving a current description of a patient, wherein the current description comprises a current medical complaint of the patient, a medical history of the patient, a current lab test result for the patient, a current physical examination result for the patient, a demographic description of the patient, a travel history of the patient, and an unrelated trauma suffered by the patient but which is unattributable to the current medical complaint of the patient;
the processor defining a cohort for the patient, wherein the cohort comprises persons who have a same medical complaint, lab test result, physical examination result, demographic description, unrelated trauma, and travel history as the patient;
the processor retrieving past accurate medical diagnoses for persons in the cohort;
the processor presenting a plurality of possible medical diagnoses for the patient, wherein the plurality of possible medical diagnoses for the patient is taken from the past accurate medical diagnoses for persons in the cohort;
the processor identifying a most likely diagnosis for the patient from the plurality of possible medical diagnoses, wherein the most likely diagnosis has a first probability of a first unacceptable outcome if improperly treated;
the processor identifying a second most likely diagnosis for the patient from the plurality of possible medical diagnoses, wherein the second most likely diagnosis has a second probability of a second unacceptable outcome if improperly treated, and wherein the second probability is greater than the first probability;
the processor directing additional tests on the patient until the second most likely diagnosis is either eliminated as a candidate diagnosis for the patient or a predetermined event occurs, wherein the predetermined event includes at least one of a group consisting of:
an expiration of a length of time to perform the additional tests,
a number of additional tests exceeding a threshold, and
a cost of additional tests exceeding a threshold; and
in response to the predetermined event occurring, the processor directing additional tests on the patient until the most likely diagnosis is eliminated.

2. The computer implemented method of claim 1, wherein the first and second unacceptable outcomes are irreversible without immediate medical intervention.

3. The computer implemented method of claim 1, wherein the first and second unacceptable outcomes are reversible only by treatments having costs that have been predetermined to be greater than a permissible upper limit.

4. The computer implemented method of claim 1, further comprising:
the processor identifying the most likely diagnosis for the patient by identifying a most frequent diagnosis from past accurate medical diagnoses for persons in the cohort.

5. The computer implemented method of claim 1, further comprising:
the processor mapping different permutations of the lab test result, physical examination result, demographic description, and travel history for persons in the cohort to past accurate medical diagnoses;
the processor identifying a best fit permutation from the different permutations for persons in the cohort, wherein the best fit permutation best fits the current description of the patient; and
the processor identifying the most likely diagnosis according to which diagnosis is mapped to the best fit permutation.

6. The computer implemented method of claim 1, further comprising:
the processor defining the demographic description of the patient by receiving inputs that describe a sex, age, ethnicity, income, and residence location of the patient.

7. The computer implemented method of claim 1, further comprising:
the processor determining that the second unacceptable outcome is a certainty regardless of any medical intervention;
the processor eliminating the second most likely diagnosis as the candidate diagnosis for the patient;
the processor identifying a third most likely diagnosis for the patient from the plurality of possible medical diagnoses, wherein the third most likely diagnosis has a third probability of a third unacceptable outcome if improperly treated, wherein the third probability is less than the second probability, and wherein the third probability is greater than the first probability; and
the processor directing additional tests on the patient until the third most likely diagnosis is eliminated as a candidate diagnosis for the patient.

8. The computer implemented method of claim 1, further comprising:
the processor identifying a third most likely diagnosis for the patient from the plurality of possible medical diagnoses, wherein the third most likely diagnosis has a third probability of a third unacceptable outcome if improperly treated, and wherein the third probability is less than the first probability; and
the processor eliminating the third most likely diagnosis as the candidate diagnosis for the patient.

9. A computer program product for deriving a medical diagnosis for a patient, the computer program product comprising:
a non-transitory computer readable storage media;
first program instructions to receive a current description of a patient, wherein the current description comprises a medical history of the patient, a current lab test result for the patient, a current physical examination result for the patient, a demographic description of the patient, and a travel history of the patient;
second program instructions to define a cohort for the patient, wherein the cohort comprises persons who have a same lab test result, physical examination result, demographic description, and travel history as the patient;
third program instructions to retrieve past accurate medical diagnoses for persons in the cohort;

fourth program instructions to present a plurality of possible medical diagnoses for the patient, wherein the plurality of possible medical diagnoses for the patient is taken from the past accurate medical diagnoses for persons in the cohort;

fifth program instructions to identify a most likely diagnosis for the patient from the plurality of possible medical diagnoses, wherein the most likely diagnosis has a first probability of a first unacceptable outcome if improperly treated;

sixth program instructions to identify a second most likely diagnosis for the patient from the plurality of possible medical diagnoses, wherein the second most likely diagnosis has a second probability of a second unacceptable outcome if improperly treated, and wherein the second probability is greater than the first probability; and seventh program instructions to direct additional tests on the patient until the second most likely diagnosis is either eliminated as a candidate diagnosis for the patient or a predetermined event occurs, wherein the predetermined event includes at least one of a group consisting of:

an expiration of a length of time to perform the additional tests, a number of additional tests exceeding a threshold, and a cost of additional tests exceeding a threshold; and eighth program instructions to, in response to the predetermined event occurring, direct additional tests on the patient until the most likely diagnosis is eliminated; and wherein the first, second, third, fourth, fifth, sixth, seventh, and eighth program instructions are stored on the non-transitory computer readable storage media.

10. The computer program product of claim 9, wherein the first and second unacceptable outcomes are irreversible without immediate medical intervention.

11. The computer program product of claim 9, wherein the first and second unacceptable outcomes are reversible only by treatments having costs that have been predetermined to be greater than a permissible upper limit.

12. The computer program product of claim 9, further comprising:

ninth program instructions to identify the most likely diagnosis for the patient by identifying a most frequent diagnosis from past accurate medical diagnoses for persons in the cohort; and wherein the ninth program instructions are stored on the non-transitory computer readable storage media.

13. The computer program product of claim 9, further comprising:

ninth program instructions to map different permutations of the lab test result, physical examination result, demographic description, and travel history for persons in the cohort to past accurate medical diagnoses;

tenth program instructions to identify a best fit permutation from the different permutations for persons in the cohort, wherein the best fit permutation best fits the current description of the patient; and eleventh program instructions to identify the most likely diagnosis according to which diagnosis is mapped to the best fit permutation; and wherein the ninth, tenth, and eleventh program instructions are stored on the non-transitory computer readable storage media.

14. The computer program product of claim 9, further comprising:

ninth program instructions to define the demographic description of the patient by receiving inputs that describe a sex, age, ethnicity, income, and residence location of the patient; and wherein the ninth program instructions are stored on the non-transitory computer readable storage media.

15. The computer program product of claim 9, further comprising:

ninth program instructions to determine that the second unacceptable outcome is a certainty regardless of any medical intervention;

tenth program instructions to eliminate the second most likely diagnosis as the candidate diagnosis for the patient;

eleventh program instructions to identify a third most likely diagnosis for the patient from the plurality of possible medical diagnoses, wherein the third most likely diagnosis has a third probability of a third unacceptable outcome if improperly treated, wherein the third probability is less than the second probability, and wherein the third probability is greater than the first probability; and twelfth program instructions to direct additional tests on the patient until the third most likely diagnosis is eliminated as a candidate diagnosis for the patient; and wherein the ninth, tenth, eleventh, and twelfth program instructions are stored on the non-transitory computer readable storage media.

16. The computer program product of claim 9, further comprising:

ninth program instructions to identify a third most likely diagnosis for the patient from the plurality of possible medical diagnoses, wherein the third most likely diagnosis has a third probability of a third unacceptable outcome if improperly treated, and wherein the third probability is less than the first probability; and tenth program instructions to eliminate the third most likely diagnosis as the candidate diagnosis for the patient; and wherein the ninth and tenth program instructions are stored on the non-transitory computer readable storage media.

17. A computer system comprising:

a processor, a computer readable memory, and a computer readable storage media;

first program instructions to receive a current description of a patient, wherein the current description comprises a medical history of the patient, a current lab test result for the patient, a current physical examination result for the patient, a demographic description of the patient, and a travel history of the patient;

second program instructions to define a cohort for the patient, wherein the cohort comprises persons who have a same lab test result, physical examination result, demographic description, and travel history as the patient;

third program instructions to retrieve past accurate medical diagnoses for persons in the cohort;

fourth program instructions to present a plurality of possible medical diagnoses for the patient, wherein the plurality of possible medical diagnoses for the patient is taken from the past accurate medical diagnoses for persons in the cohort;

fifth program instructions to identify a most likely diagnosis for the patient from the plurality of possible medical diagnoses, wherein the most likely diagnosis has a first probability of a first unacceptable outcome if improperly treated;

sixth program instructions to identify a second most likely diagnosis for the patient from the plurality of possible medical diagnoses, wherein the second most likely diagnosis has a second probability of a second unacceptable outcome if improperly treated, and wherein the second probability is greater than the first probability; and seventh program instructions to direct additional tests on the patient until the second most likely diagnosis is either eliminated as a candidate diagnosis for the patient or a predetermined event occurs, wherein the predetermined event includes at least one of a group consisting of an expiration of a length of time to perform the additional tests, a number of additional tests exceeding a threshold, and a cost of additional tests exceeding a threshold; and eighth program instructions to, in response to the predetermined event occurring, direct additional tests on the patient until the most likely diagnosis is eliminated; and wherein the first, second, third, fourth, fifth, sixth, seventh, and eighth program instructions are stored on the non-transitory computer readable storage media for execution by the processor via the computer readable memory.

18. The computer system of claim 17, further comprising:

ninth program instructions to map different permutations of the lab test result, physical examination result, demographic description, and travel history for persons in the cohort to past accurate medical diagnoses;

tenth program instructions to identify a best fit permutation from the different permutations for persons in the cohort, wherein the best fit permutation best fits the current description of the patient; and eleventh program instructions to identify the most likely diagnosis according to which diagnosis is mapped to the best fit permutation; and wherein the ninth, tenth, and eleventh program instructions are stored on the computer readable storage media for execution by the processor via the computer readable memory.

19. The computer system of claim 17, further comprising:

ninth program instructions to determine that the second unacceptable outcome is a certainty regardless of any medical intervention;

tenth program instructions to eliminate the second most likely diagnosis as the candidate diagnosis for the patient;

eleventh program instructions to identify a third most likely diagnosis for the patient from the plurality of possible medical diagnoses, wherein the third most likely diagnosis has a third probability of a third unacceptable outcome if improperly treated, wherein the third probability is less than the second probability, and wherein the third probability is greater than the first probability; and twelfth program instructions to direct additional tests on the patient until the third most likely diagnosis is eliminated as a candidate diagnosis for the patient; and wherein the ninth, tenth, eleventh, and twelfth program instructions are stored on the computer readable storage media for execution by the processor via the computer readable memory.

20. The computer system of claim 17, further comprising:

ninth program instructions to identify a third most likely diagnosis for the patient from the plurality of possible medical diagnoses, wherein the third most likely diagnosis has a third probability of a third unacceptable outcome if improperly treated, and wherein the third probability is less than the first probability; and tenth program instructions to eliminate the third most likely diagnosis as the candidate diagnosis for the patient; and wherein the ninth and tenth program instructions are stored on the computer readable storage media for execution by the processor via the computer readable memory.

* * * * *